United States Patent
Schnupp et al.

(10) Patent No.: US 8,429,988 B2
(45) Date of Patent: Apr. 30, 2013

(54) SOIL-CEMENT SAMPLING DEVICE

(75) Inventors: Keith Schnupp, Ashburn, VA (US); Allen Stanton, Lake Isabella, MI (US)

(73) Assignee: Schnabel Foundation Company, Sterling, VA (US)

(*) Notice: Subject to any disclaimer, the term of this patent is extended or adjusted under 35 U.S.C. 154(b) by 366 days.

(21) Appl. No.: 12/944,395

(22) Filed: Nov. 11, 2010

(65) Prior Publication Data

US 2012/0118082 A1    May 17, 2012

(51) Int. Cl.
  *G01N 1/12* (2006.01)
  *G01N 1/04* (2006.01)

(52) U.S. Cl.
  USPC ............... 73/864.58; 73/864.59; 73/864.44

(58) Field of Classification Search ............... 73/864.44, 73/864.53, 864.55, 864.56, 864.59
  See application file for complete search history.

(56) References Cited

U.S. PATENT DOCUMENTS

| | | | |
|---|---|---|---|
| 1,109,446 A * | 9/1914 | Melberg | 175/49 |
| 1,570,647 A | 1/1926 | Steigh et al. | |
| 3,047,081 A | 7/1962 | Pitcher | |
| 3,176,053 A * | 3/1965 | Di Stasio | 264/31 |
| 3,527,439 A * | 9/1970 | Lawmaster | 249/164 |
| 4,365,784 A * | 12/1982 | De Stasio | 249/139 |
| 4,518,051 A | 5/1985 | Sollie et al. | |
| 4,588,036 A | 5/1986 | Desrochers et al. | |
| 4,729,437 A | 3/1988 | Zapico | |
| 4,907,659 A | 3/1990 | Ludwig | |
| 5,562,169 A | 10/1996 | Barrow | |
| 5,618,997 A * | 4/1997 | Owens et al. | 73/864.55 |
| 6,047,782 A | 4/2000 | Ballard et al. | |
| 6,510,743 B2 * | 1/2003 | McAfee et al. | 73/803 |
| 6,736,224 B2 | 5/2004 | Kinsella | |
| 7,431,107 B2 | 10/2008 | Hill et al. | |
| 2003/0205408 A1 | 11/2003 | Lee et al. | |
| 2009/0000822 A1 | 1/2009 | Myrick | |

FOREIGN PATENT DOCUMENTS

| | | |
|---|---|---|
| DE | 3200881 | 7/1983 |
| JP | 07-324583 | 12/1995 |
| JP | 2005-082998 | 3/2005 |

* cited by examiner

Primary Examiner — Hezron E Williams
Assistant Examiner — Nathaniel Kolb
(74) Attorney, Agent, or Firm — Banner & Witcoff, Ltd.

(57) ABSTRACT

A soil-cement sampling device and method of sampling soil-cement is provided. The soil-cement sampling device may include an inner tube arranged within an outer tube. The inner tube may be removably connected to the outer tube and may be split into two longitudinal sections removably connected to each other. The inner and outer tubes may be inserted into a recently mixed soil-cement mixture before it hardens and a sample of the soil-cement mixture may be collected in the inner tube after it hardens. Once the sample hardens, the inner tube may be removed from the outer tube and the longitudinal sections may be separated to expose the soil-cement sample for inspection and testing.

22 Claims, 8 Drawing Sheets

SOIL-CEMENT SAMPLING DEVICE

BACKGROUND

Soil-mixing or jet-grouting are ground improvement techniques used to increase the strength and reduce the permeability of soils in-situ. The desired compressive strength of this treated soil or soil-cement may be between 50 and 500 psi. In order to ensure that the desired consistency of the soil is obtained and to provide general quality control, the soil-cement is sampled, inspected and tested. Tests to determine the unconfined compressive strength and permeability are routinely performed and the quality of the mixing is determined by inspection of the recovered samples. Obtaining quality, continuous soil-cement samples is difficult, particularly when the soil-cement has relatively low strength, less than 150 psi.

Conventional methods of sampling soil cement include methods similar to core drilling used to recover samples of soft rocks. However, these methods can damage the sample and affect the integrity of the soil-cement sample obtained. Further, for low strength soil cements (e.g., less than 150 psi), or soil cements with gravel, it is difficult to obtain any representative samples by coring. For instance, low strength soil-cements are weak and are not strong enough to survive the coring process. The sample disintegrates inside the core barrel as the core bit tries to advance through the soil-cement. When gravel is present in the soil-cement it is significantly stronger than the soil-cement surrounding it and it requires considerable more effort to core the gravel than the soil-cement matrix. While trying to core through the gravel the weak soil-cement is eroded away from the gravel and soon loose pieces of gravel are rotating in the core barrel. These loose pieces of gravel completely destroy the soil-cement core.

Another method of obtaining a soil-cement sample involves wet grab sampling of the recently mixed soil-cement at depth. While still fluid, a volume of the soil-cement is recovered and placed into molds for curing and later testing. However, the curing of the soil-cement does not take place in the ground (i.e., the actual conditions of the soil-cement in use) and thus could affect results. Further, wet grab samples do not provide a continuous treated soil-cement sample for an entire depth of the soil improvement. Accordingly, it can not be relied on to evaluate the quality of the mixing.

Accordingly, a device and method of obtaining a continuous soil-cement sample over the depth of the improved soil would be advantageous.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

A soil-cement sampling device and method of collecting a soil-cement sample using the soil-cement sampling device are presented. The soil-cement sampling device may include an inner tube positioned within an outer tube. The inner tube and outer tube may be assembled as a unit. A connection assembly at the top of the unit enables the inner and outer tube to be inserted into the recently mixed soil-cement prior to hardening. The connection assembly may be disconnected from the outer tube enabling the inner tube to be removed from the outer tube.

In some examples, a cutting shoe may be fixed to the outer tube. The inside diameter of the shoe may be equal to the inside diameter of the inner tube. A circular plate with an outside diameter similar to the outer tube and a hole or aperture having approximately the same diameter as the inside diameter of the inner tube is positioned between the shoe and the bottom of the outer tube. In some examples the outer tube, circular plate and cutting shoe are secured together as unit, such as by welding. The aperture in the cutting shoe and plate may facilitate the flow of the soil-cement mixture into the inner tube as the sampling device is inserted into the recently mixed soil-cement. A seal or gasket may be arranged between the inner tube and the plate to prevent the soil-cement mixture from entering a void created between the inner tube and the outer tube. The connection assembly is able to force the inner tube down and compress the seal between the inner tube and the circular plate. In some arrangements, the inner tube may include two or more longitudinal sections that are removably connected to form the inner tube. In some arrangements, each split longitudinal section may have flanges that allow the two split sections to be connected to form a longitudinal section of the inner tube. The joints of the longitudinal sections may, in some examples, be sealed with a gasket.

Additional aspects of the invention relate to collecting a soil-cement sample. In some arrangements, the inner tube and outer tube are inserted into the recently mixed soil-cement (e.g., wet soil-cement mixture) prior to hardening (e.g., setting). The soil-cement mixture may be collected in the inner tube as a sample of the mixture. The sample may be allowed to cure. Once the sample has cured, the inner tube may be removed from the outer tube and the longitudinal sections may be separated to expose the soil-cement sample for inspection and later testing.

The foregoing summary of aspects of the invention, as well as the following detailed description of various arrangements, is better understood when read in conjunction with the accompanying drawings, which are included by way of example, and not by way of limitation with regard to the claimed invention.

BRIEF DESCRIPTION OF THE DRAWINGS

The present disclosure is illustrated by way of example and not limited in the accompanying figures in which like reference numerals indicate similar elements.

FIG. 7 is the connection arrangement or assembly of FIG. 6 as seen rotated 90°.

The reader is advised that the attached drawings are not necessarily drawn to scale.

DETAILED DESCRIPTION OF THE DRAWINGS

Aspects of the present invention relate to a soil-cement sampling device and method of using the device. The device may be used, in some examples, to obtain a continuous sample of the soil-cement mixture. As will be described more fully below, the soil-cement sampling device may include an inner tube and an outer tube. The two-tube device may be inserted into a recently mixed soil-cement mixture prior to hardening and a soil-cement sample may be collected in the inner tube of the two-tube device. The soil-cement sample may cure in-situ in the inner tube and may then be removed from the device for inspection and testing of the sample. Additional details of the soil-cement sampling device and methods of using the device are described more fully below.

Figure 1:
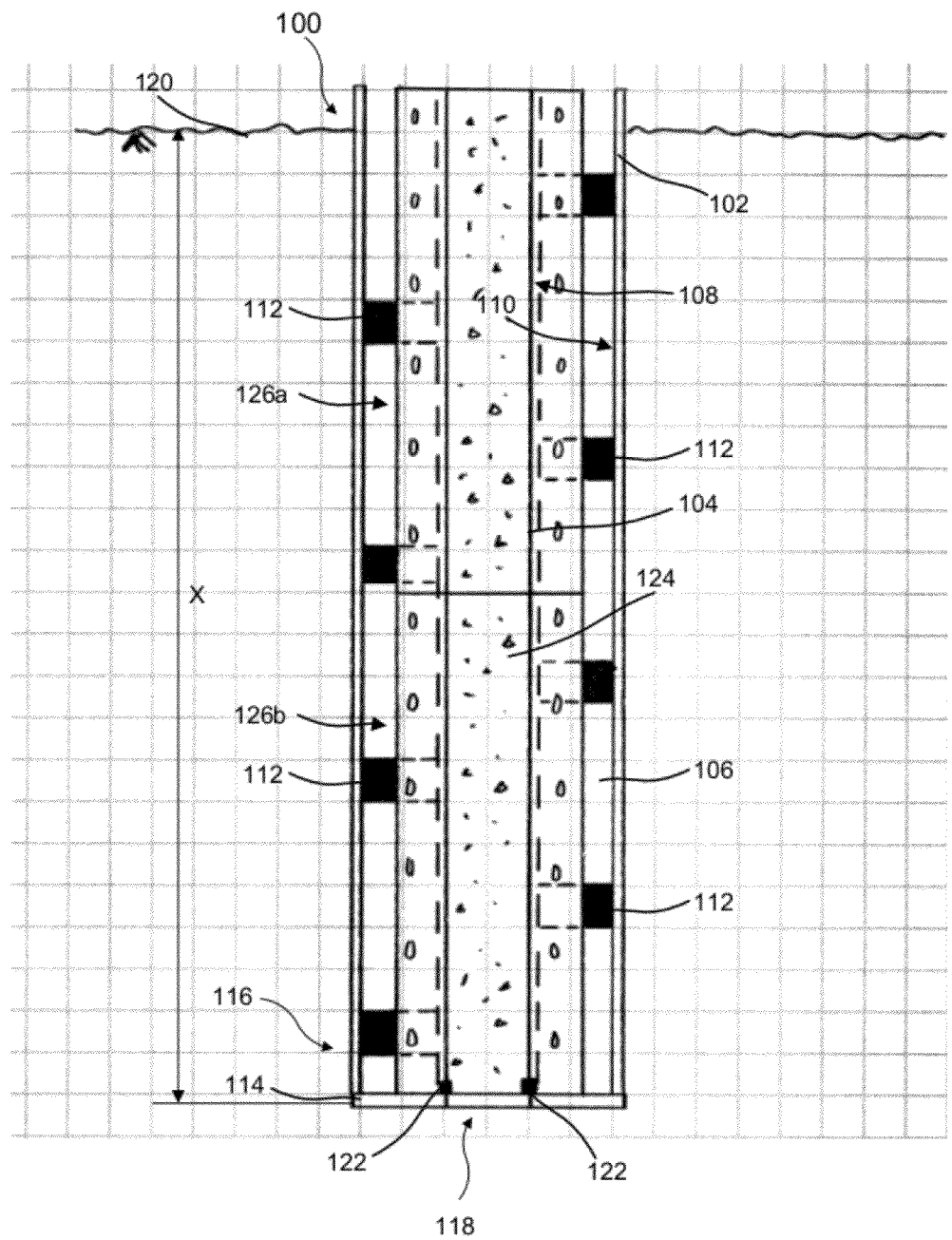
FIG. 1 is a cross-sectional view of one example soil-cement sampling device according to at least some aspects described herein.

FIG. 1 illustrates one example of a two-tube soil-cement sampling device 100 according to one or more aspects described herein. As mentioned above, the two-tube sampling device 100 may include an outer tube 102 and an inner tube 104, positioned within the outer tube 102. The inner and outer tubes 104, 102, respectively, have shapes corresponding to each other or substantially similar to each other. For instance, the inner tube 104 and outer tube 102 may both have a substantially cylindrical cross section. In other examples, the inner tube 104 and outer tube 102 may have various other cross-sections, including hexagonal, pentagonal, octagonal, square, rectangular, and the like. In still other examples, the inner tube 104 and outer tube 102 may have somewhat different cross-sections. For instance, the inner tube 104 may be cylindrical while the outer tube 102 is octagonal, or vice versa. Various combinations of shapes of the inner tube 104 and outer tube 102 may be used without departing from the invention.

In some examples, a void 106 may exist between an outer wall 108 of the inner tube 104 and an inner wall 110 of the outer tube 102. In some arrangements, the inner tube 104 may be centered within the outer tube 102 such that the void 106 created is substantially the same around the entire circumference of the outer wall 108 of the inner tube 104 and the inner wall 110 of the outer tube 102. For instance, one or more spacers or positioners 112 may be provided between the inner tube 104 and the outer tube 102 to aid in maintaining the central position of the inner tube 104 within the outer tube 102. In some arrangements, the spacers or positioners 112 may be connected to the inner tube 104 or outer tube 102, such as via welding, mechanical fasteners such as screws, bolts, etc., and the like. Further, the spacers 112 may, in some examples, extend around the entire inner wall 110 of the outer tube 102 or outer wall 108 of the inner tube 104. Alternatively, as shown in FIG. 1, the spacers 112 may be positioned at various points along the inner wall 110 of the outer tube 102 or the outer wall 108 of the inner tube. In some examples, the spacers 112 may be staggered.

The inner tube 104 may be positioned within the outer tube 102 such that relative movement may occur between the inner tube 104 and outer tube 102. For instance, the inner tube 104 may be removed from the soil-cement sampling device 100 while the outer tube 102 may remain embedded in the hardened soil-cement 120. Additionally or alternatively, although spacers or other positioners 112 may be used to maintain the position of the inner tube 104 within the outer tube 102, the positioners 112 may, in some examples, permit some relative movement of the inner tube 104 within the outer tube 102. Alternatively, the positioners 112 may be arranged to prevent any lateral movement of the inner tube 104 within the outer tube 102, while permitting the removal of the inner tube 104 from the outer tube 102 (and thus the sampling device 100) to allow for inspection of the soil-cement sample.

In some examples, the two-tube soil-cement sampling device 100 may further include a plate 114 connected to an end of the sampling device 100. For instance, a plate 114 may be connected to a bottom end 116 (i.e., the end being inserted into the soil-cement mixture), such as via welding, mechanical or threaded fasteners, etc. and may be connected to the outer tube 102 of the soil-cement sampling device 100. In some examples, the plate 114 may be shaped to correspond to the shape of the outer tube 102 and may be sized to cover the entire end of the outer tube 102 (and, thus, the inner tube 104 positioned within the outer tube 102, as well). That is, if the outer tube 102 is substantially cylindrical, the plate 114 may be substantially circular and may be sized to cover the bottom end of the outer tube 102.

The plate 114 may further include an aperture 118 formed therein and extending entirely through the plate 114. This aperture 118 may correspond to the size and position of the inner tube 104 positioned within the outer tube 102 and may permit the soil-cement sample to enter the inner tube 104 when the soil-cement sampling device 100 is inserted into the soil-cement mixture (i.e., the aperture 118 may be aligned with an open bottom end of the inner tube 104). In some examples, the aperture 118 may be between 2.0 and 10.0 inches. A seal or gasket 122 may be positioned between the plate 114 and the inner tube 104 to prevent soil-cement mixture from entering the void 106 between the inner tube 104 and the outer tube 102 (i.e., to ensure the soil-cement mixture enters only the inner tube 104 where the sample can be collected, removed and examined) and may extend around the aperture 118. The seal or gasket 122 may be formed of natural or synthetic rubber, various polymers, fiberglass, metal, cork, silicone, neoprene, and the like. In some arrangements, the inner tube 104 may be connected (e.g., removably connected) to the outer tube 102 at a top end (not shown in FIG. 1), as will be discussed more fully below. This connection may compress the gasket 122 to prevent soil-cement from entering the void between the outer tube 102 and the inner tube 104.

Figure 2:
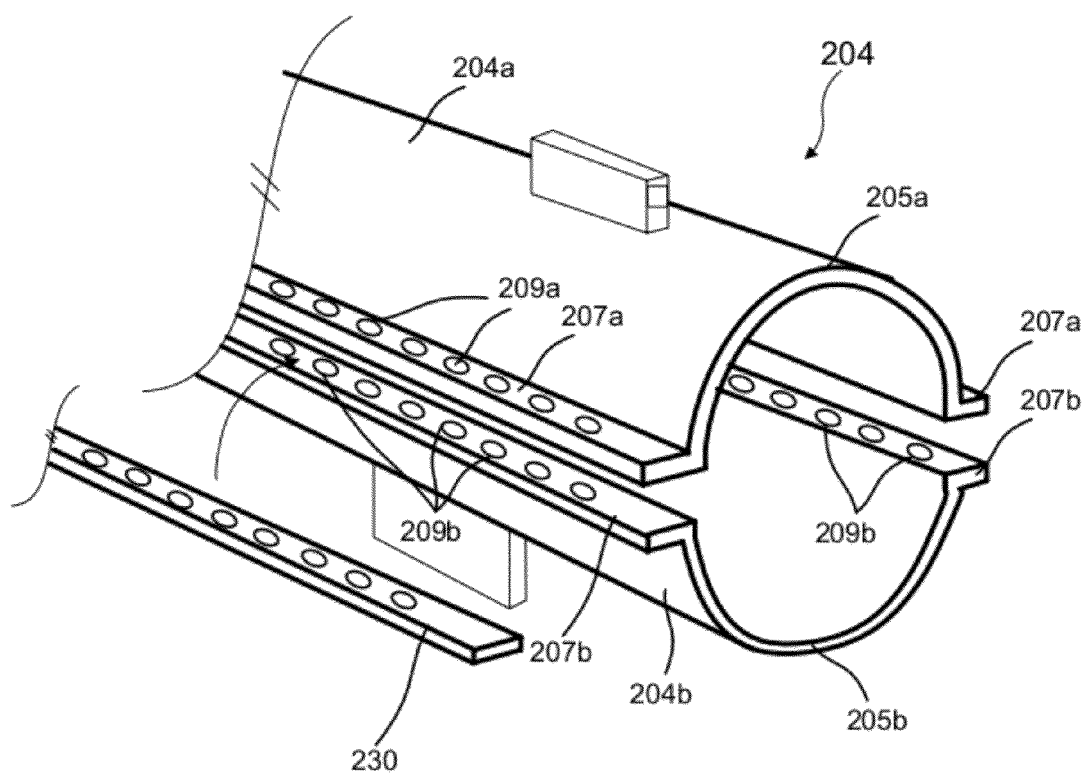
FIG. 2 is a perspective view of one example flanged split tube that may be used as an inner tube of the soil-cement sampling device according to at least some aspects described herein.

In some examples, the inner tube 104 may be split longitudinally (or vertically when the sampling device 100 is in an upright position) to form two halves of the inner tube 104 which may be removably connected. For instance, the inner tube 104 may be formed of flanged split tube. FIG. 2 illustrates one example of flanged split tube 204. As shown, each longitudinal section or half 204a, 204b generally includes an arced portion 205a, 205b that, when joined with the second half will form the cylindrical tube. The arced portions 205a, 205b includes a flange 207a, 207b extending outward from each end and extending along the length of each half 204a, 204b. The upper flanged portions 207a include a plurality of apertures 209a that correspond to apertures 209b formed in the lower flanged portions 207b of the mating half of the tube. A plurality of screws, bolts, other fasteners, clips, or collars (not shown) may extend through the apertures 209a, 209b to removably connect the two halves of the tube. Accordingly, the inner tube 104 may be non-destructively separated into two halves in order to examine a soil-cement sample contained therein or to recover portions for testing, as will be discussed more fully below. In some examples, a seal or gasket 230 may be inserted between mating flanged portions 207a, 207b to aid in sealing the tube to prevent moisture or other debris from entering the sample and/or to prevent soil-cement from the sample leaking into the void between the inner tube and the outer tube. Although a gasket 230 is shown on one side of the tube, a second gasket on the opposite set of flanges may also be used. Although the flanged split tube shown generally includes two halves, three or more longitudinal sections may be removably connected to form the inner tube without departing from the invention. Further, the inner tube may be formed without the flanges and connected using other methods of connection, as will be discussed more fully below.

With further reference to FIG. 1, the cross-section of the soil-cement sampling device 100 is shown in an in-use position. That is, the sampling device 100 has been inserted into a soil-cement mixture (e.g., below grade 120). Upon insertion of the sampling device into the soil-cement mixture, a portion of the mixture will transfer into the inner tube 104 to form the soil-cement sample 124. The soil-cement sample 124 is shown arranged within the inner tube 104.

The soil-cement sampling device 100 may be used to obtain continuous soil-cement samples at varying depths. For instance, the soil-cement sampling device 100 may be sectioned so that the vertical length of the soil-cement sampling device may be adjusted. For instance, vertical sections (such as sections 126a, 126b) of inner tube 104 and outer tube 102 may be connected to form a soil-cement sampling device 100 that may be adjusted between 2 feet in length and 100 feet in length. Accordingly, the device 100 may extend into the soil-cement mixture a depth of X feet (as indicated in FIG. 1) below grade, where X may be between 2 feet and 100 feet. In some examples, the sections of inner tube 104 and outer tube 102 being used may be 10 foot sections of tube. Accordingly, the soil-cement sampling device 100 in these arrangements may be between 10 feet and 100 feet in length and may be adjustable in 10 foot increments. In some examples, a plate may be arranged between the vertical sections 126a, 126b in order to provide increased strength during removal of the inner tube.

In still other examples, inner tube 104 and outer tube 102 sections may vary in length, thus providing a soil-cement sampling device 100 that may extend between 2 feet and 100 feet and may be adjustable in numerous varying increments. For example, sections of inner tube 104 and outer tube 102 may be 1 foot in length, 2 feet in length, 5 feet in length, 10 feet in length, etc. Accordingly, the overall length of the soil-cement sampling device 100 may be adjusted to any lengths by connecting sections of the inner tube 104 and outer tube 102 having various section lengths.

In some examples, the sections of inner tube 104 and outer tube 102 may be connected via threads formed on the sections themselves (e.g., a male thread section end may mate with a corresponding female thread on another section). Other known coupling arrangements may be used to join vertical sections of the inner tube and/or outer tube without departing from the invention. The coupling arrangement used may provide increased strength, for instance, for the inner tube to support the tube during removal of the inner tube and sample.

In some arrangements, the length of a vertical section of inner tube 104 and a length of a vertical section of outer tube 102 may vary within a sampling device 100. This arrangement may result in the connection points or joints of adjoining vertical sections of the inner tube 104 being offset from the joints of the outer tube 102. In other examples, a length of the vertical section may vary along each half (such as longitudinal section 204a, 204b in FIG. 2) such that the joints at which each vertical section meet on a longitudinal section (e.g., 204a) are offset from the joints of the mating longitudinal section 204b. For instance, the first longitudinal section 204a may have a 5 foot section connected to a 10 foot section which is then connected to another 10 foot section. The joints may then be arranged at 5 feet and 15 feet. The mating longitudinal section 204b may have a 10 foot section connected to a 10 foot section which is then connected to a 5 foot section. The joints on section 204b would then be positioned at 10 feet and 20 feet and would thus be offset from the joints on mating longitudinal section 204a. This may aid in providing additional stability, strength, etc. to the sampling device 100.

The outer tube 102 may be formed of any suitable material strong enough for insertion into the soil-cement mixture. For instance, the outer tube 102 may be formed of steel. In some examples, the outer diameter of the outer tube 102 may be between 3 inches and 12 inches. The thickness of the outer tube 102 may range between 0.2 inches and 1.0 inches.

The inner tube 104 may be formed of materials such as steel, aluminum, polyvinyl chloride (PVC) pipe, and the like. An arrangement using PVC pipe (e.g., shallow depth samples), unsplit PVC pipe may be inserted into the outer tube and may be split upon removal to examine the sample and thus would not be reused. The material of which the inner tube 104 is formed may be selected to ensure the inner tube 104 is strong enough to enable the cured soil-cement sample 124 and the inner tube 102 to be removed from the outer tube. For instance, once the soil-cement sample 124 cures within the sampling device 100, the inner tube 104, along with the cured soil-cement sample 124, are lifted out of the outer tube 102. This removal may require the inner tube 104 to be formed of a material that will maintain its shape, structure, etc. in order to maintain the quality, integrity, etc. of the sample 124. Further, the outer tube 102 and inner tube 104 may be formed of the same or substantially similar materials or, alternatively, may be formed of different materials. In some examples, the inner tube may be separated upon removal (such as separated into vertical sections) in order to shorten the length of inner tube and sample to ease removal. The shorter sections of inner tube may be removed more easily than longer sections while maintaining the integrity of the entire sample along the length of the inner tube.

In some arrangements, the outer diameter of the inner tube 104 may between 2 inches and 10 inches. The thickness of the inner tube 104 may also vary between 0.2 and 1.0 inches.

Figure 3:
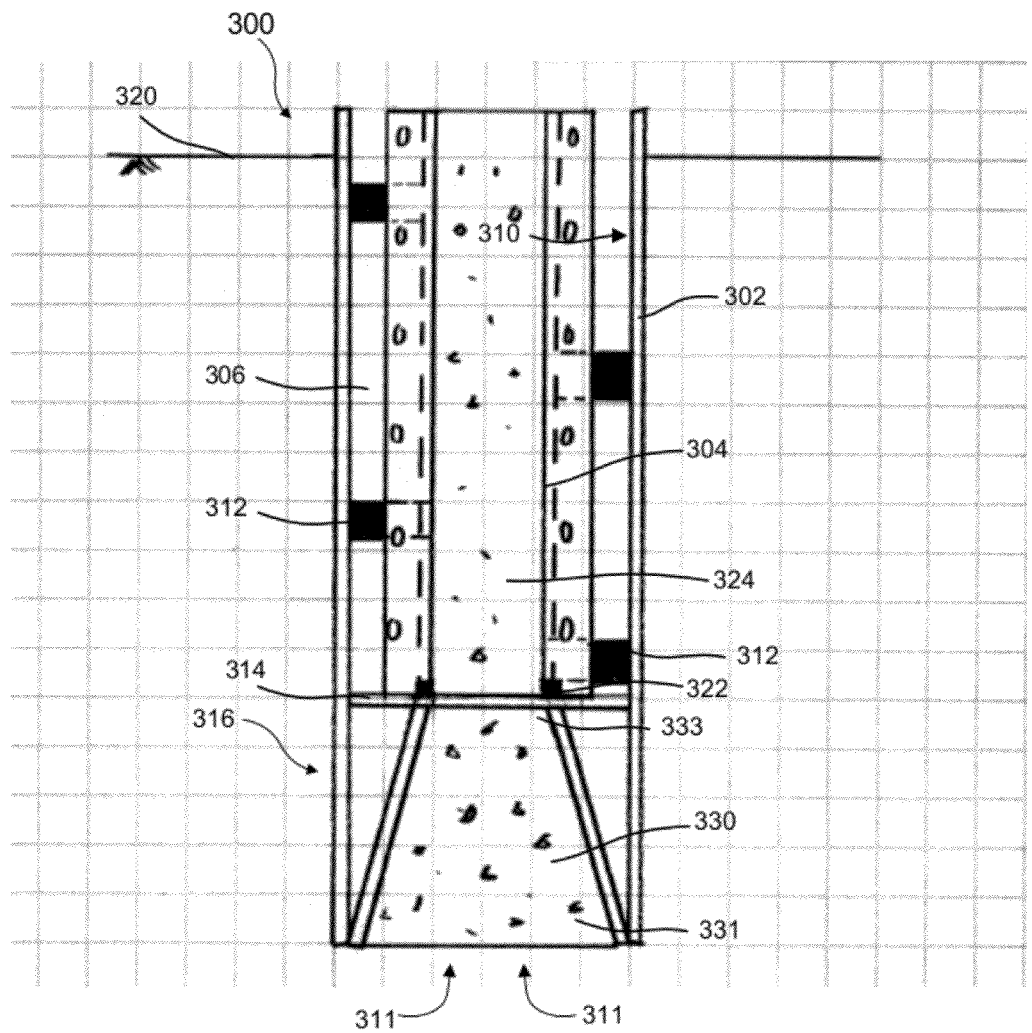
FIG. 3 is a cross-sectional view of another example soil-cement sampling device according to at least some aspects described herein.

FIG. 3 illustrates another example soil-cement sampling device 300 according to aspects described herein. Similar to the arrangement of FIG. 1, the sampling device 300 includes an outer tube 302 and an inner tube 304 positioned within the outer tube 302. In some examples, the inner tube 304 may be centered within the outer tube 302 and spacers or positioners 312 arranged in the void 306 between the inner tube 304 and the outer tube 302 may be used to aid in maintaining the position of the inner tube 304 relative to the outer tube 302, similar to the arrangements discussed above.

The soil-cement sampling device 300 of FIG. 3 further includes a cutting shoe 330 arranged at a lower end 316 of the soil-cement sampling device 300. In some examples, the cutting shoe 330 may be conical in shape and may have a greater diameter at a bottom end 331 (i.e., the end contacting the soil-cement mixture) than at a top end 333 of the cutting shoe 330 (i.e., the end in contact with the inner tube of the sampling device 300) to act as a funnel and direct the soil-cement mixture upward, into the inner tube 304. Arrows 311 indicate the flow of the semi-liquid soil-cement mixture upward, into the cutting shoe 330 and further into the inner tube 304.

In some arrangements, the cutting shoe 330 may be connected to the circular plate 314 arranged at near the bottom end 316 of the sampling device 300. For instance, the cutting shoe 330 may be connected to the plate 314 via welding, fasteners, etc. In the arrangement shown, the circular plate 314 may be connected to the outer tube 302 on the interior of the outer tube 302 and a portion of the outer tube 302 may extend downward, beyond the circular plate 314. Accordingly, in these arrangements and as shown in FIG. 3, the cutting shoe 330 may be arranged within (e.g., internal to) the outer tube 302 such that the outer tube 302 extends downward, to the bottom 331 of the cutting shoe 330. The cutting shoe 330 may then be contained within the outer tube 302 and, in some examples, may be connected to the outer tube 302 along an inner surface 310 of the outer tube 302. For example, a bottom portion 331 of the cutting shoe 330 may be connected to the inner surface 310 of the outer tube 302, such as via welding, to aid in maintaining the position of the cutting shoe 330 and to aid in directing the soil-cement mixture into the cutting shoe 330 and inner tube 304, rather than around an exterior surface of the cutting shoe 330 or into the void 306 between the inner tube 304 and the outer tube 302.

Alternatively, the cutting shoe 330 may be connected to the plate 314 positioned near a bottom 316 of the sampling device 300 and may extend beyond a bottom of the outer tube (not shown in FIG. 3). That is, the cutting shoe 330 may be positioned external to the outer tube 302, rather than internal to it, as discussed above.

Similar to the arrangement of FIG. 1, a seal or gasket 322 may be arranged at a lower portion of the inner tube 304 and/or between the inner tube 304 and the bottom plate 314 in order to prevent soil-cement mixture from entering the void between the inner tube 304 and the outer tube 302.

Figure 4:
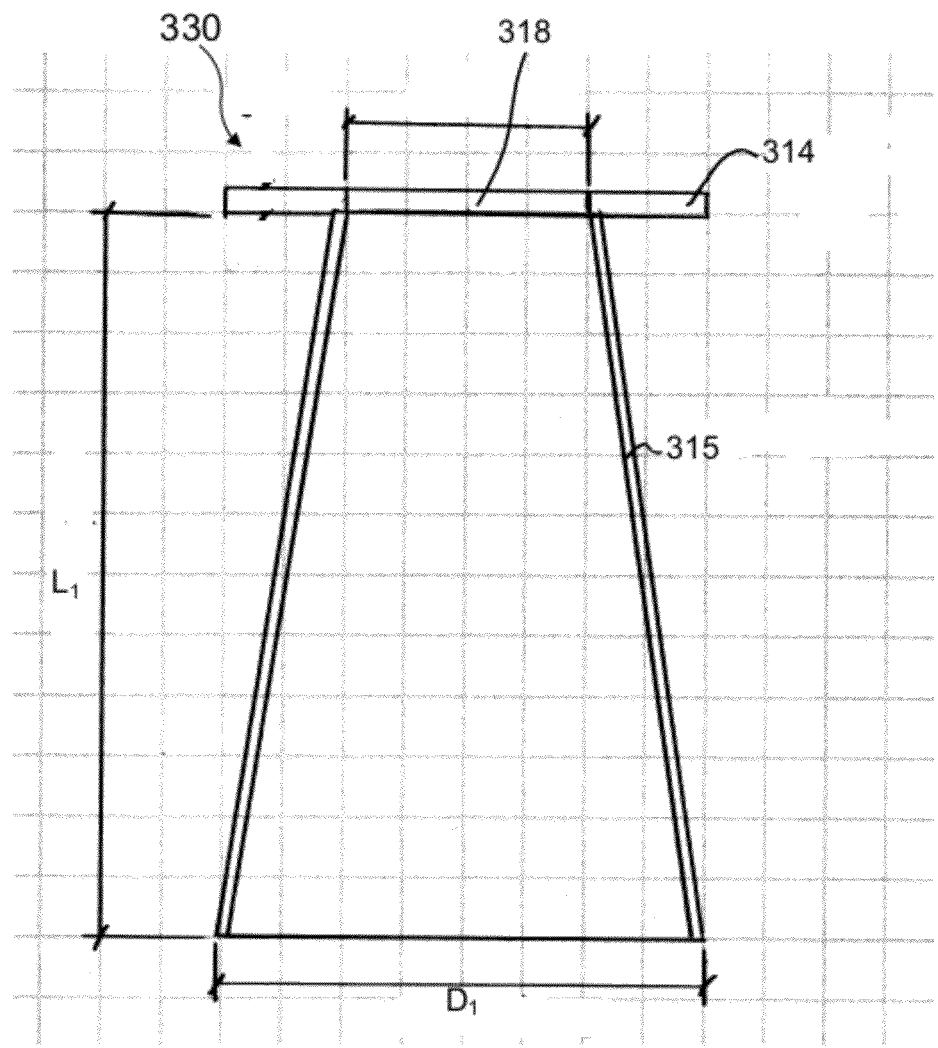
FIG. 4 is an enlarged view of a cutting shoe that may be used in conjunction with the soil-cement sampling device according to at least some aspects described herein.

FIG. 4 is an enlarged view of the cutting shoe 330 of the soil-cement sampling device 300. As shown, the cutting shoe 330 is conical in shape and may be connected to the bottom plate 314 of the soil-cement sampling device 300, as discussed above. In some arrangements, the cutting shoe 330 may be approximately 8 to 12 inches in length (e.g., along length $L_1$. The cutting shoe 330 may be formed of any suitable material, such as steel, and, in some examples, may have an outer diameter $D_1$ along a bottom edge that corresponds to the inner diameter of the outer tube 302. For instance, in arrangements in which the cutting shoe 330 is positioned internal to the outer tube 302, the bottom surface of the cutting shoe may have a diameter $D_1$ equal to or substantially equal to the inner diameter of the outer tube 302. The thickness of the material forming the sidewalls 315 of the cutting shoe 330 may be between 0.2 and 0.75 inches.

In any of the above-described arrangements, the cutting shoe 330 may be connected to the plate 314 and positioned to correspond to the aperture 318 formed in the plate 314 and corresponding to an open end of the inner tube 304. For instance, the open top edge of the cutting shoe 330, the aperture 318 formed in the plate 314 and the open bottom end of the inner tube 304 may be substantially aligned to aid in permitting the flow of soil-cement mixture upward, into the inner tube 304 to act as a sample 324.

Figure 5:
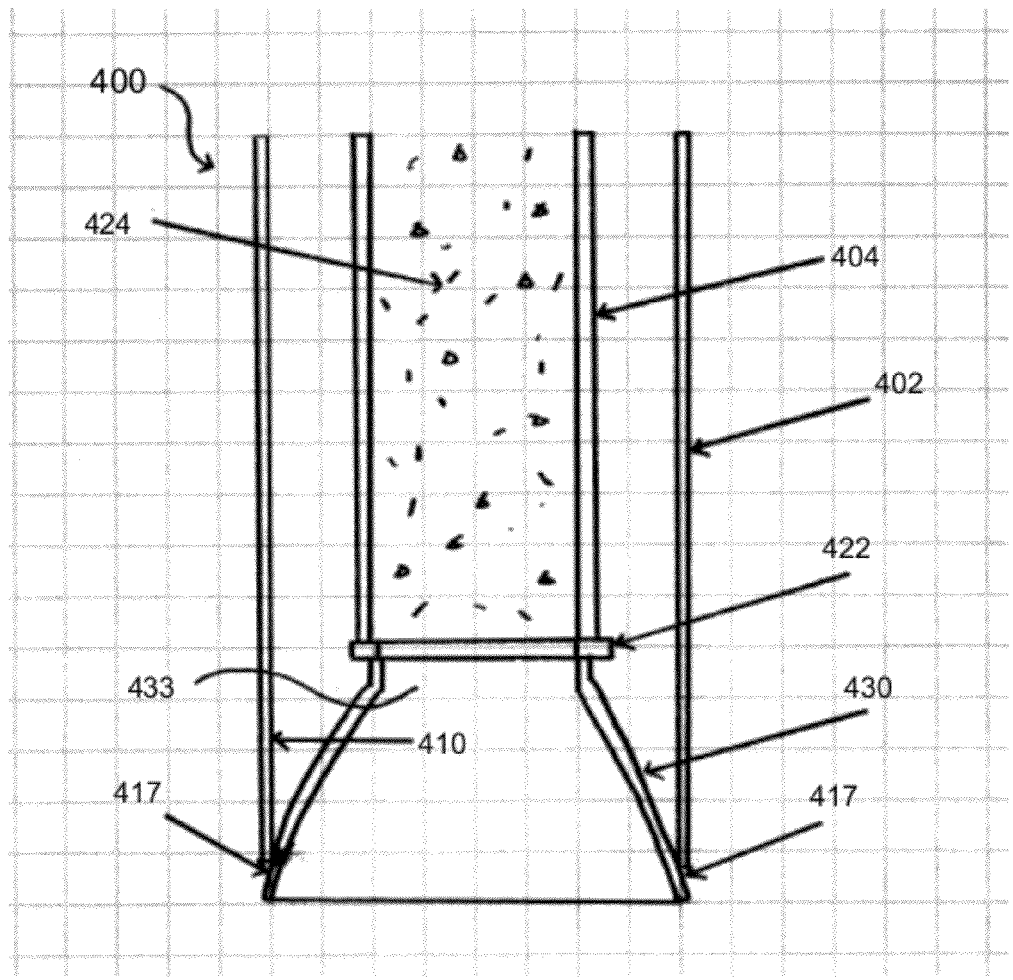
FIG. 5 is a cross-sectional view of another cutting shoe arrangement according to at least some aspects described herein.

FIG. 5 illustrates yet another example of a cutting shoe 430 arranged at a bottom end of the soil-cement sampling device 400. Similar to the arrangements described above, the soil-cement sampling device 400 includes an outer tube 402 and an inner tube 404 arranged within the outer tube 402. The inner tube 404 may have a smooth outer surface and, as shown in FIG. 5, may be a straight tube that does not include any flanges. In arrangements in which the inner tube 404 does not include flanges to connect the longitudinal sections of the tube, various other methods of connection may be used. For instance, straps, clamps, welding, etc. (either alone or in combination) may be used to removably connect the longitudinal sections of the inner tube 404. These non-flanged inner tube arrangements may permit use of an outer tube 402 having a smaller inner diameter because the outer tube would not have to accommodate the space associated with the flange. This may reduce costs, particularly on job sites having multiple soil-cement testing sites.

In some examples, a sealant may be used to aid in preventing moisture or debris from entering the inner tube or from soil-cement leaking into the void between the inner tube 404 and the outer tube 402.

The cutting shoe 430 is connected to the bottom end of the outer tube 402. For instance, the cutting shoe 430 may be connected to an inner surface 410 of the outer tube 402 (as shown in FIG. 5) using welds or other suitable methods of connection (such as at locations 417). In some examples, the cutting shoe 430 may be connected to the outer tube 402 using a threaded connection. In the arrangement shown, the cutting shoe 430 is positioned on an interior of the outer tube 402 and a top portion 433 of the cutting shoe 430 may mate with a bottom edge of the inner tube 404 via a seal or gasket 422. A bottom plate similar to that shown and discussed above could be used too. That is, the gasket 422 may be compressed between the cutting shoe 430 and the inner tube 404 when the inner tube 404 and outer tube 402 are connected at a top region (i.e., above grade), as will be described more fully below. In some examples, the mating portions of the cutting shoe and inner tube may be machined to mate and seal such that no additional seal or gasket may be desired.

Figure 6:
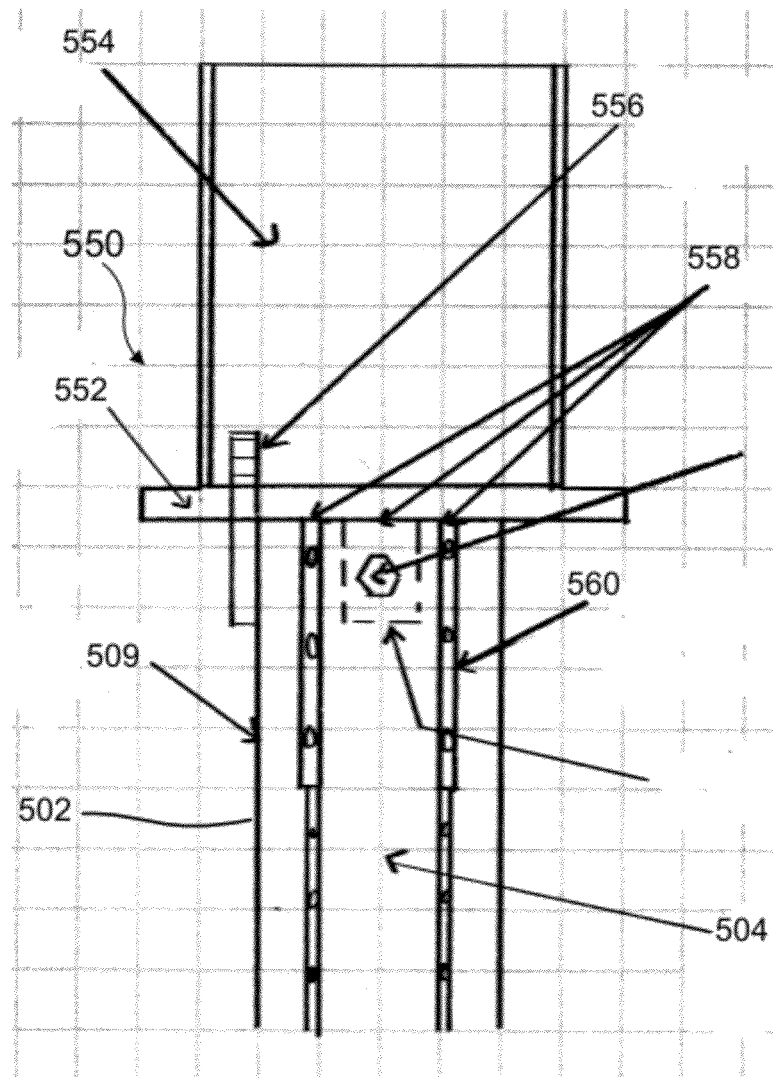
FIGS. 6 and 7 are cross-sectional views of a connection arrangement or assembly configured to removably connect the inner tube of the soil-cement sampling device to the outer tube accordingly to at least some aspects described herein.
Figure 7:
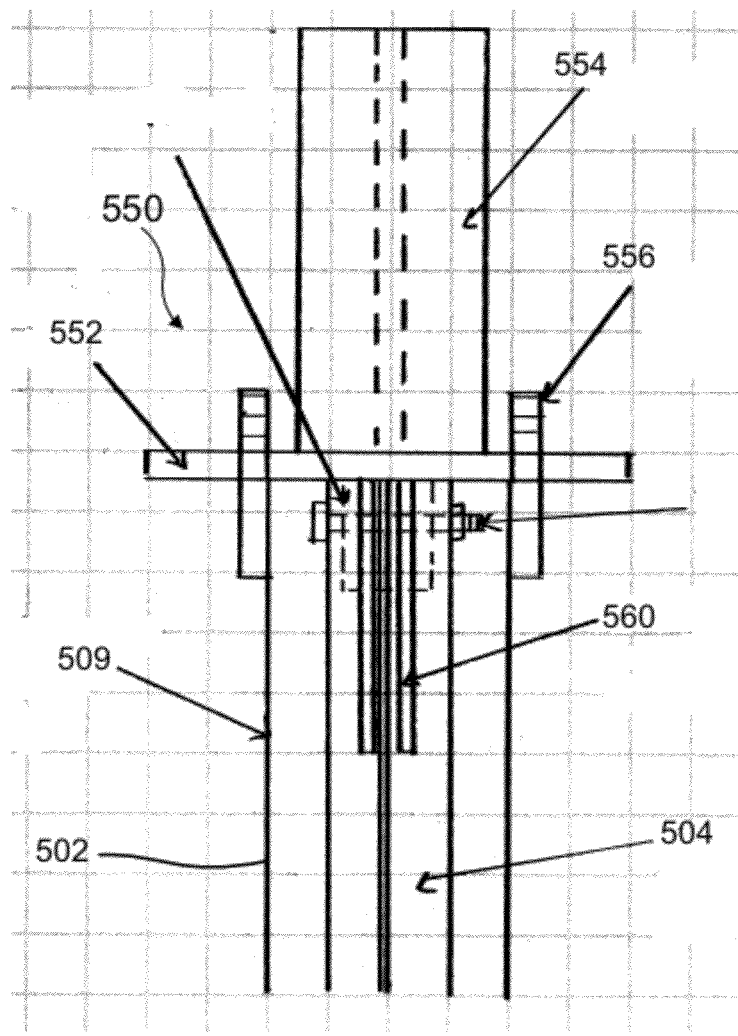

FIGS. 6 and 7 illustrate one example arrangement for fixing the location of the inner tube 504 with respect to the outer tube 502 and to apply a force to compress the gasket (such as gasket 122, etc.) and/or securely position the inner tube 504 to the cutting shoe to prevent soil-cement from entering the space between the inner tube 504 and the outer tube 502. FIG. 7 is a cross-sectional view of the arrangement of FIG. 6 rotated 90°. The positioning arrangement 550 includes a plate 552 connected to the inner tube 504 and having a beam or plate 554 extending upward, substantially perpendicular to the plate 552. The plate 552 may be square, circular, etc. as desired. A plurality of threaded studs, or other threaded fasteners 556 may extend through the plate 552 and may be connected to an outer surface 509 of the outer tube 502. For instance, a portion of the thread of the threaded rods, or other fasteners 556 may be welded to the outer surface 509 of the outer tube 502. In some examples, the plate 552 (and thus the beam or plate 554) may be connected to the inner tube 504, such as via welds 558 along a top surface of the inner tube 504. Accordingly, removal of the inner tube 504 from the outer tube 502 may include loosening the bolts or other fasteners 556, attaching a crane or other lifting device to the plate 554 and raising plate 552 and the inner tube 504 with the soil-cement sample upward until the sample is completely removed from the outer tube 502.

The top positioning arrangement 550 may also include a plurality of straps 560 extending downward from the plate 552 to the inner tube 504. The straps may be connected (such as by welding) to the plate 552 and may be bolted to the inner tube. These straps and bolts may provide additional strength during removal of the inner tube.

The positioning arrangement 550 described above may be used to removably fix the inner tube 504 with respect to the outer tube 502 during insertion into the soil-cement. For instance, the threaded fasteners 556 may be used to tighten the plate 552 onto the outer tube 502 while forcing the inner tube 504 to compress the seal or gasket (such as gasket 122) located at the bottom of the inner tube 504, or to securely fit the inner tube 504 to the cutting shoe (such as cutting shoe 330 in FIG. 3). The seal or tight fit between the bottom of the inner tube 504 and the cutting shoe may prevent the soil-cement mixture from entering the void between the inner tube 504 and the outer tube 502.

The connection arrangement 550 described may be used with any soil-cement sampling device arrangement described herein. Further, the connection arrangement 550 is merely one example of an arrangement that may be used to removably fix the inner tube to the outer tube. Various other methods of connection may be used without departing from the invention.

Figure 8:
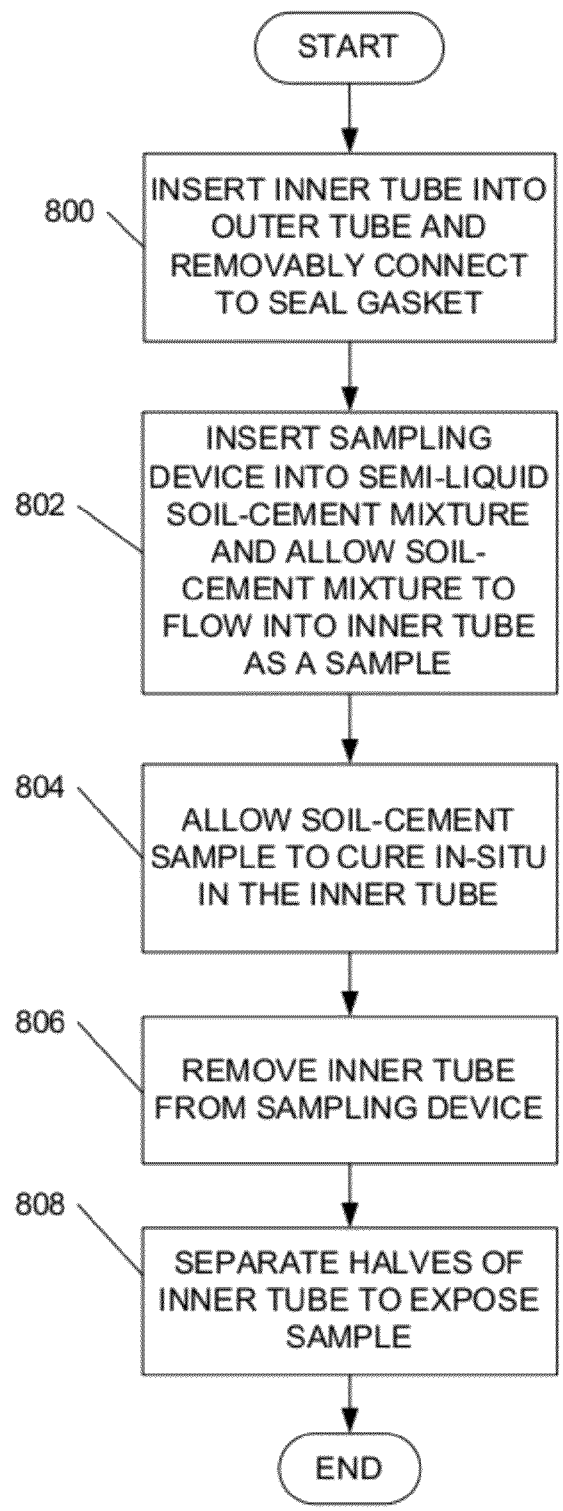
FIG. 8 is a flowchart illustrating an example method of sampling a soil-cement mixture using the soil-cement sampling device according to at least some aspects described herein.

FIG. 8 illustrates one example method of assembling the soil-cement sampling device and obtaining a sample. In step 800, the inner tube may be inserted into the outer tube and removably connected thereto. Removable connection of the inner tube to the outer tube may be performed using the positioning arrangement discussed above, or other suitable methods of connection. In addition, connection of the inner tube to the outer tube may compress the gasket positioned at a bottom of the inner tube to prevent the soil-cement mixture from entering the void between the outer surface of the inner tube and the inner surface of the outer tube.

In step 802, the soil-cement sampling device (including both the inner tube and outer tube) may be inserted into a recently mixed (i.e., wet) soil-cement mixture. In some arrangements, the soil-cement sampling device may be forced or driven into the soil-cement mixture. As the soil-cement sampling device is lowered into the soil-cement mixture, the soil-cement mixture will be forced upward and into the inner tube. In some examples, a cutting shoe may be connected to the bottom of the sampling device in order to aid in funneling the soil-cement mixture into the inner tube. The soil-cement mixture within the inner tube is the soil-cement sample that will be extracted, as will be discussed below.

In step 804 the soil-cement sample within the inner tube is allowed to cure in-site in the inner tube. The sample may cure for several days. The duration of the time needed for curing may be specified by the quality assurance or quality control requirements of the project or job site on which the sample is being collected. In some arrangements, the soil-cement may cure between 3 days and 60 days. Once the sample has cured for the specified time, the inner tube may be removed from the sampling device in step 806. Removal of the inner tube may include use of a hoist, lift, crane, etc. to aid in removal, depending upon the size, length, weight, etc. of the inner tube and sample. Removal of the inner tube may include raising the inner tube upward, out of the outer tube while the outer tube may remain in place within the hardened soil-cement mixture. In some arrangements, the outer tube may remain in the soil-cement mixture permanently. Removal of the inner tube may also include positioning the inner tube against a beam or other structure to provide support to the inner tube and sample. For instance, once the inner tube is removed, it may be arranged against a beam to provide support as the inner tube is being positioned for inspection of the sample.

In step 808 the flanged portions of the inner tube may be separated (e.g., non-destructively separated) in order to expose the cured soil-cement sample within the inner tube. Exposure of the sample may permit inspection of the sample along the entire length of the sample and, in some arrangements, the entire depth of the soil-cement mixture at the site.

Although the invention has been defined using the appended claims, these claims are illustrative in that the invention may be intended to include the elements and steps described herein in any combination or sub combination. Accordingly, there are any number of alternative combinations for defining the invention, which incorporate one or more elements from the specification, including the description, claims, and drawings, in various combinations or sub combinations. It will be apparent to those skilled in the relevant technology, in light of the present specification, that alternate combinations of aspects of the invention, either alone or in combination with one or more elements or steps defined herein, may be utilized as modifications or alterations of the invention or as part of the invention. It may be intended that the written description of the invention contained herein covers all such modifications and alterations.

What is claimed is:

1. A soil-cement sampling device, comprising:
a first cylindrical tube having a top end and a bottom end;
a second cylindrical tube positioned within the first cylindrical tube and removably connected to the first cylindrical tube;
a plate arranged at the bottom end of the first cylindrical tube, the plate including an aperture extending through the plate and aligned with an open end of the second cylindrical tube positioned within the first cylindrical tube; and
a seal arranged between the plate and the open end of the second cylindrical tube;
wherein the second cylindrical tube, when connected to the first cylindrical tube, is configured to recover a soil-cement sample when the sampling device is inserted into recently mixed soil-cement before it hardens, wherein the seal prevents the soil-cement sample from entering a void formed between an interior surface of the first cylindrical tube and an exterior surface of the second cylindrical tube, and wherein the second cylindrical tube is configured for removal from the first cylindrical tube after the soil-cement has hardened.

2. The soil-cement sampling device of claim 1, wherein the second cylindrical tube is split along a longitudinal axis and includes a first longitudinal section removably connected to a second longitudinal section.

3. The soil-cement sampling device of claim 2, further including a seal arranged between the first longitudinal section and the second longitudinal section.

4. The soil-cement sampling device of claim 1, further including a top assembly removably connected to the second cylindrical tube and configured to be adjustably connected to the top end of first cylindrical tube by threaded rods when in the upright position.

5. The soil-cement sampling device of claim 4, wherein the top assembly is adjustably connected to the top end of the first cylindrical tube by threaded rods.

6. The soil-cement sampling device of claim 4, wherein the top assembly and the second cylindrical tube are forced downward with respect to the first cylindrical tube compressing the seal between the plate and the bottom end of the second cylindrical tube when the top assembly and the second cylindrical tube are connected.

7. The soil-cement sampling device of claim 1, further including a plurality of spacers configured to maintain a position of the second cylindrical tube within the first cylindrical tube.

8. A soil-cement sampling device, comprising:
a first cylindrical tube having an inner diameter;
a second cylindrical tube arranged within the first cylindrical tube and removably connected to the first cylindrical tube and having an outer diameter smaller than the inner diameter of the first cylindrical tube to form a void between the first cylindrical tube and the second cylindrical tube, the second cylindrical tube being non-destructively separable along a longitudinal axis;

a cutting shoe arranged within the first cylindrical tube, the cutting shoe being positioned vertically below the second cylindrical tube when the soil-cement sampling device is in an upright position; and a seal arranged between a bottom of the second cylindrical tube and the cutting shoe when the soil-cement sampling device is in an upright position;

wherein the second cylindrical tube, when connected to the first cylindrical tube, is configured to recover a soil-cement sample when the soil-cement sampling device is inserted into recently mixed soil-cement before it hardens, wherein the seal prevents the soil-cement sample from entering the void formed between the first cylindrical tube the second cylindrical tube, and wherein the second cylindrical tube is configured for removal from the first cylindrical tube after the soil-cement has hardened.

9. The soil-cement sampling device of claim 8, wherein the cutting shoe is conical in shape.

10. The soil-cement sampling device of claim 8, wherein the cutting shoe is connected to an inner surface of the first cylindrical tube.

11. The soil-cement sampling device of claim 10, wherein the cutting shoe is welded to the first cylindrical tube.

12. The soil-cement sampling device of claim 10, wherein the cutting shoe is threaded onto the first cylindrical tube.

13. The soil-cement sampling device of claim 8, wherein an outer diameter of a bottom portion of the cutting shoe is substantially equal to the inner diameter of the first cylindrical tube.

14. The soil-cement sampling device of claim 8, wherein the soil-cement sampling device is configured to be inserted into a recently mixed soil-cement mixture before it hardens and the second cylindrical tube is configured to be removed from the soil-cement sampling device when the soil-cement mixture cures and hardens.

15. The soil-cement sampling device of claim 7, wherein the second cylindrical tube includes a first longitudinal section and a second longitudinal section.

16. The soil-cement sampling device of claim 15, wherein the first and second longitudinal sections including a flanged portion for connecting the first longitudinal section to the second longitudinal section.

17. The soil-cement sampling device of claim 15, wherein the first and second longitudinal sections are removably connected to each other using at least one of straps, bands, clamps, threaded fasteners, and welds.

18. The soil-cement sampling device of claim 8, further including a third cylindrical tube configured to be vertically connected to the first cylindrical tube and a fourth cylindrical tube configured to be vertically connected to the second cylindrical tube to extend an overall length of the soil-cement sampling device.

19. A method of sampling a soil-cement mixture, comprising:

positioning a second cylindrical tube in a first cylindrical tube and removably connecting the second cylindrical tube to the first cylindrical tube which compresses a gasket at a bottom end of the second cylindrical tube, the second cylindrical tube having at least two longitudinal sections removably connected to each other;

inserting the removably connected first cylindrical tube and second cylindrical tube into the soil-cement mixture to collect a sample of the soil-cement mixture within the second cylindrical tube;

curing the sample of the soil-cement mixture collected within the second cylindrical tube in-situ;

removing the second cylindrical tube from the first cylindrical tube; and non-destructively separating the two longitudinal sections of the second cylindrical tube to expose the collected, cured soil-cement sample.

20. The method of claim 19, wherein connecting the first cylindrical tube to the second cylindrical tube includes compressing the gasket between the second cylindrical tube and a plate connected to the first cylindrical tube.

21. The method of claim 19, wherein positioning the second cylindrical tube in the first cylindrical tube includes centering the second cylindrical tube within the first cylindrical tube.

22. The method of claim 19, further including connecting a conical cutting shoe to the first cylindrical tube.

* * * * *